United States Patent
Petyaev

(10) Patent No.: US 7,939,275 B2
(45) Date of Patent: May 10, 2011

(54) METHODS FOR DETECTION OF CHLAMYDIA IN SAMPLES

(75) Inventor: Ivan Petyaev, Cambridge (GB)

(73) Assignee: Cambridge Theranostics Limited, Babraham, Cambridge (GB)

( * ) Notice: Subject to any disclaimer, the term of this patent is extended or adjusted under 35 U.S.C. 154(b) by 653 days.

(21) Appl. No.: 11/885,048

(22) PCT Filed: Feb. 24, 2006

(86) PCT No.: PCT/GB2006/000655
§ 371 (c)(1),
(2), (4) Date: Apr. 11, 2008

(87) PCT Pub. No.: WO2006/090162
PCT Pub. Date: Aug. 31, 2006

(65) Prior Publication Data
US 2009/0029395 A1   Jan. 29, 2009

(30) Foreign Application Priority Data

Feb. 25, 2005   (GB) .................................. 0503939.1

(51) Int. Cl.
*G01N 33/53* (2006.01)
(52) U.S. Cl. ....... 435/7.2; 435/7.1; 435/7.32; 424/263.1
(58) Field of Classification Search .................. None
See application file for complete search history.

(56) References Cited

FOREIGN PATENT DOCUMENTS
WO        WO 03/017992        3/2003

OTHER PUBLICATIONS

International Search Report of PCT/GB2006/000655 dated Apr. 25, 2006.

*Primary Examiner* — Jennifer E Graser
(74) *Attorney, Agent, or Firm* — Nixon & Vanderhye, P.C.

(57) ABSTRACT

This invention relates to assays for *Chlamydia* which include the step of inactivating lipid oxidation activity in a biological sample, such as a blood or serum sample. This inactivation improves the detection of *Chlamydia* antigens or anti-*Chlamydia* antibodies. Methods and materials for the detection of *Chlamydia* and *Chlamydial* infection are provided.

24 Claims, 2 Drawing Sheets

METHODS FOR DETECTION OF CHLAMYDIA IN SAMPLES

Figure 1:
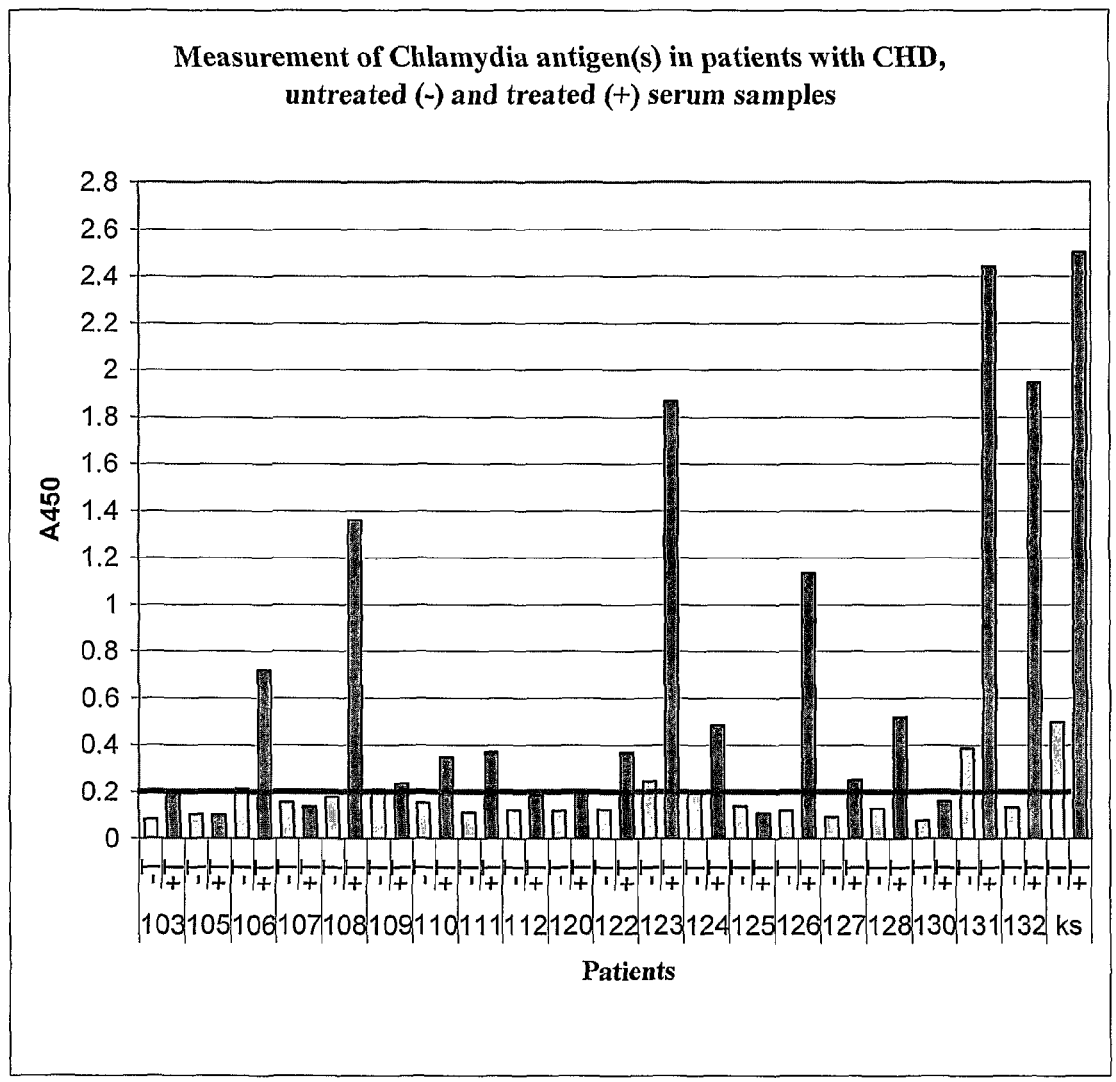

This application is the U.S. national phase of International Application No. PCT/GB2006/000655 filed 24 Feb. 2006 which designated the U.S. and claims priority to Great Britain Patent Application No. 0503939.1 filed 25 Feb. 2005, the entire contents of each of which are hereby incorporated by reference.

This invention relates to the detection of *Chlamydia* in samples of blood or serum. This may be useful, for example, in testing an individual for *Chlamydia* infection.

*Chlamydiae* are obligate intracellular microorganisms which parasitize eukaryotic cells and are ubiquitous throughout the animal kingdom. *Chlamydiae* have a biphasic developmental cycle, which has intracellular and extracellular stages, each stage having distinct morphological forms. In intracellular stages, *Chlamydiae* may form a metabolically-active, replicating organism known as the reticulate body (RB) or a persistent, non-replicating organism known as the cryptic phase. In infectious extracellular stages, *Chlamydiae* may form a metabolically-inactive body known as the elementary body (EB).

EBs are small (300-400 nm), infectious, spore-like forms which are metabolically inactive and non-replicating. They are usually found in acellular environments. EBs are resistant to a variety of physical insults, including enzyme degradation, sonication and osmotic pressure. Under oxidizing conditions in acellular environments within the host, the outer membrane of EBs is relatively impermeable and resistant to inactivation. EBs are thus well suited to survive long enough outside of their hosts to be transmitted to a new host in the form of a droplet nuclei (Theunissen et al., Applied Environmental Microbiology, 59:2589-2593 (1993)) or a fomite (Fasley et al., The Journal of Infectious Diseases, 168:493-496 (1993))

Infection by members of the genus *Chlamydiae* induces a significant inflammatory response at the cellular level. Clinically, the initial infection is frequently varied in symptomatology and may even be asymptomatic. Once fully established, *Chlamydiae* are difficult to eradicate, with frequent relapse following antibiotic therapy. Evidence also indicates that the *Chlamydia* may become dormant and are then shed in quantities too few to reliably detect by culture. Chlamydial infections are therefore often chronic and persistent and there is a need for reliable, accurate methods for the diagnosis of infection.

The present inventor has recognised that inactivating or abrogating lipid oxidation activity in a biological sample, such as a blood or serum sample, increases the reliability of assays for *Chlamydia* in the sample.

One aspect of the invention provides a method of measuring the level of a first *Chlamydia* binding pair member in a sample comprising;
  abrogating lipid oxidation activity in the sample, and
  determining the binding of a first *Chlamydia* binding pair member in the treated sample to a second *Chlamydia* binding pair member,
  the amount of binding after said treatment being indicative of the level of the first *Chlamydia* binding pair member in the sample.

The first *Chlamydia* binding pair member may be one of a *Chlamydia* antigen and an anti-*Chlamydia* antibody and the second *Chlamydia* binding pair member may be the other of a *Chlamydia* antigen and an anti-*Chlamydia* antibody.

For example, the first *Chlamydia* binding pair member may be an anti-*Chlamydia* antibody and the second *Chlamydia* binding pair member may be a *Chlamydia* antigen.

A method of measuring anti-*Chlamydia* antibody levels in a sample may comprise;
  abrogating lipid oxidation activity in said sample, and;
  determining the binding of antibodies in the treated sample to a *Chlamydia* antigen,
  the amount of binding after said treatment being indicative of the level of anti-*Chlamydia* antibodies in the sample.

In other embodiments, the first *Chlamydia* binding pair member may be a *Chlamydia* antigen and the second *Chlamydia* binding pair member may be an anti-*Chlamydia* antibody.

A method of measuring *Chlamydia* antigen levels in a sample may comprise;
  abrogating lipid oxidation activity in said sample, and
  determining the binding of *Chlamydia* antigen in the treated sample to an anti-*Chlamydia* antibody,
  the amount of binding after said treatment being indicative of the level of *Chlamydia* antigen in the sample.

The presence or amount of *Chlamydia* antigen or anti-*Chlamydia* antibody in a sample obtained from an individual may be indicative of the presence of *Chlamydia* infection in the individual.

A sample may comprise plasma or serum from the individual, and may be, for example, a blood, serum or plasma sample. Methods for obtaining, storing and preparing suitable samples from an individual are well known in the medical practice. For example, a test sample of serum may be obtained by extracting blood from an individual and isolating the serum from the extracted blood. Suitable extraction methods include centrifugation to separate serum and plasma from cellular material.

A *Chlamydia* antigen may be any immunogen or immunogenic component of a *Chlamydia* cell i.e. a molecule from *Chlamydia* which evokes or is capable of evoking an immune response in a mammal against the *Chlamydia* cell. In other words, the *Chlamydia* antigen is a component of a *Chlamydia* cell that is capable of specifically binding to antibodies raised against the *Chlamydia* cell. In some embodiments, the *Chlamydia* antigen may be LPS.

In some embodiments, the *Chlamydia* antigen may be an antigen on the surface of a *Chlamydia* cell. In other words, the binding of antibodies to a Chlamydial cell may be determined in the present methods. A Chlamydial cell may be a cell from a species belonging to the *Chlamydia psittaci* group. The *Chlamydia psittaci* group includes *Chlamydia psittaci* and *Chlamydia pneumoniae*.

The binding of antibodies to a *Chlamydia* antigen may be determined by any appropriate means or assay format. Tagging with individual reporter molecules is one possibility. For example, a second antibody which binds to antibodies in the sample, or a *Chlamydia* cell or antigen may be tagged with a reporter molecule. The reporter molecules may directly or indirectly generate detectable, preferably measurable, signals. Where required, linkage of reporter molecules may be direct or indirect, covalent, e.g. via a peptide bond, or non-covalent. Linkage via a peptide bond may be as a result of recombinant expression of a gene fusion encoding binding molecule (e.g. antibody) and reporter molecule.

Reporters include fluorochromes such as fluorescein, rhodamine, phycoerythrin and Texas Red, chromogenic dyes such as diaminobenzidine, macromolecular colloidal particles or particulate material such as latex beads that are coloured, magnetic or paramagnetic, and biologically or chemically active agents that can directly or indirectly cause detectable signals to be visually observed, electronically detected or otherwise recorded.

Biologically or chemically active agents include enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Further examples include horseradish peroxidase and chemiluminescence. Any such method may be used to determine the binding of the antibody to *Chlamydia* antigen.

The signals generated by individual antibody-reporter conjugates may be used to derive quantifiable absolute or relative data of the relevant antibody binding in samples (normal and test).

Immunological assays are well-known in the art and many suitable formats are available, for example ELISA, Western blotting, microimmunofluorescence (MIF), Biacore®, (Biacore, Upsala, Sweden), immunoprecipitation or immuno-turbidimetry, agglutination, for example erythrocyte-, latex- or other polymer-based agglutination, immunohistochemistry, immunoelectrophoresis, antibody-based affinity chromatography, IDEIA® (Boots-Celltech) and other red-ox amplifying diagnostic systems.

In some preferred embodiments, a sandwich assay format may be employed. For example, sandwich assay may employ a capture antibody which binds *Chlamydia* antigen in the sample and a second labelled anti-*Chlamydia* antibody which detects the presence of antigen bound to the capture antibody.

Alternatively, a sandwich assay may employ a capture *Chlamydia* antigen or cell and a labelled antibody, for example a labelled anti-human IgG antibody, which detects the presence of anti-*Chlamydia* antibodies bound to the antigen.

A capture antibody, *Chlamydia* antigen or *Chlamydia* cell may be immobilised, for example, by attachment to an insoluble support or solid surface. The support may be in particulate or solid form and may include a plate, a test tube, beads, a ball, a filter or a membrane. Methods for fixing antibodies to insoluble supports are known to those skilled in the art. An antibody may be immobilised, for example, to isolate endogenous antibodies from the sample.

A non-immobilised component of an assay (i.e. a component which is free in solution) such as an antibody or *Chlamydia* antigen or cell may comprise a detectable label as described above. For example, the antibody may be labelled with a fluorophore such as FITC or rhodamine, a radioisotope, or a non-isotopic labeling reagent such as biotin or digoxigenin; components containing biotin may be detected using "detection reagents" such as avidin conjugated to any desirable label such as a fluorochrome.

The mode of determining binding is not a feature of the present invention and those skilled in the art are able to choose a suitable mode according to their preference and general knowledge.

Lipid oxidation activity of a sample may be antibody-mediated lipid oxidation activity, for example oxidation which is catalysed by abzymes (see, for example, WO03/017992, WO03/019196 and WO03/019198), in particular anti-*Chlamydia* abzymes. Abzymes may include anti-*Chlamydia* IgG molecules which oxidize lipids. The oxidation of plasma lipoproteins by abzymes is a known risk factor, for example, in the development of conditions such as atherosclerosis.

Any suitable physical or chemical treatment may be used to reduce or abrogate lipid oxidation activity in the sample. In some embodiments, the sample may be physically treated to reduce or abrogate lipid oxidation.

For example, the sample may be heated. Preferably, the sample is heated in accordance with any temperature regimen that inactivates lipid oxidation activity but does not affect binding properties of specific binding pair members, i.e. antibodies or antigens, in the sample. A suitable temperature regimen may include heating the sample to 70° C. for at least 1, at least 2, at least 3, at least 5, or at least 10 minutes; heating the sample to 56° C. for at least 15, at least 20, at least 30, at least 45, or at least 60 minutes; or heating the sample to 37° C. for at least 8 hours, at least 12 hours, at least 24 hours, or at least 48 hours.

Other physical treatments may be used to inactivate lipid oxidation activity without affecting the binding properties of specific binding pair members.

The sample may be subjected to repetitive freeze-thaw cycles, for example two or more cycles of freezing followed by thawing. The sample may be subjected to prolonged storage, for example at least 4 days at 0° C. to 4° C., at least 2 or at least 3 months at −10° or at least 4 or at least 6 months at −20° C. The sample may be subjected to high-energy ultrasound, microwave, UV, gamma radiation or any other electro magnetic waves.

The suitability of a treatment or regimen may be determined by treating a sample and measuring the lipid oxidation activity and *Chlamydia*-binding antibody content of the sample after treatment, as described herein. A suitable treatment or regimen for use in the present methods inactivates lipid oxidation activity but does not affect the binding properties of anti-*Chlamydia* antibodies or *Chlamydia* antigens.

In other embodiments, the sample may be chemically treated to inactivate lipid oxidation activity. For example, the sample may be treated with one or more abzyme inactivating agents.

Inactivating agents may include low pH antioxidants (i.e. inhibits oxidation reactions at pH5.5), hydroxyl radical scavengers, 'electron trappers' such as crown ethers and steroids, 'electron cushions' such as polyvinyl-based polymers, 'electron sinks', such as ubiquinones and $Q_8$, copper chelators and calcium chelators.

Examples of suitable inactivating agents include ascorbic acid, acetyl salicylic acid, sodium azide, catechins, including catechin gallate, DMSO, azithromycin, haemoglobin, telithromycin ketek, or derivatives, analogues and salts of any of these.

In other embodiments, an inactivating agent may be a bacterial cell, for example a cell from probiotic bacteria such as lactobacilli, or a product of such a cell.

The efficacy of a treatment in inactivating lipid oxidation activity in sample may be determined by measuring the lipid oxidation activity of abzymes, for example IgG obtained from a patient atheroma, before and after being subjected to the treatment. Any convenient method of determining lipid oxidation may be used. Many methods for determining lipid oxidation are known in the art and may be used to determine the reduction or abrogation of lipid oxidation activity in a sample. Suitable methods are, for example, described in CRC Handbook of Methods for Oxygen Radical Research, CRC Press, Boca Raton, Fla. (1985), Oxygen Radicals in Biological Systems. Methods in Enzymology, v. 186, Academic Press, London (1990); Oxygen Radicals in Biological Systems. Methods in Enzymology, v. 234, Academic Press, San Diego, New York, Boston, London (1994); and Free Radicals. A practical approach. IRL Press, Oxford, New York, Tokyo (1996) In preferred embodiments, oxidation is determined by determining the production (i.e. the presence or amount) of a lipid oxidation product, which may include aldehydes such as malondialdehyde (MDA), (lipid) peroxides, diene conjugates or hydrocarbon gases.

Another aspect of the invention provides a method of preparing a sample for measurement of anti-*Chlamydia* antibody or *Chlamydia* antigen levels in the sample, the method comprising;

reducing or abrogating lipid oxidation activity in said sample.

Following the reduction or abrogation of lipid oxidation activity, the levels of anti-*Chlamydia* antibody or *Chlamydia* antigen in the sample may be measured using conventional immunoassay techniques.

The sample from the individual may be further treated to inhibit or reduce complement activity. In some embodiments, the sample may be treated with a complement inhibitor. Inhibitors of complement activity are well known in the art and include, for example, $Ca^{2+}$ chelators such as EGTA or EDTA, thymidine kinase inhibitors, including catechins such as epigallocatechin gallate (EGCG), polysaccharides such as zymosan, peptidyl molecules such as CD46, CD55, CD59, pexelizumab, eculizumab, compstatin, Cobra venom, antibodies against C1q and other components or intermediates of complement cascade, and fragments of these antibodies, and compounds which imitate the functions and properties of the complement cascade.

In other embodiments, the sample may be treated with a procedure or regimen which inhibits complement activity. Suitable procedures include heating the sample, for example to 56° C. for 30 minutes, or 70° C. for 2-5 minutes, or other temperature regimen that inactivates complement. Other physical procedures, such as ultrasound shock, irradiation and/or laser treatment, may also be used.

Various further aspects and embodiments of the present invention will be apparent to those skilled in the art in view of the present disclosure. All documents mentioned in this specification are incorporated herein by reference in their entirety.

The invention encompasses each and every combination and sub-combination of the features that are described above.

Certain aspects and embodiments of the invention will now be illustrated by way of example and with reference to the figures described above and tables described below.

Figure 2:
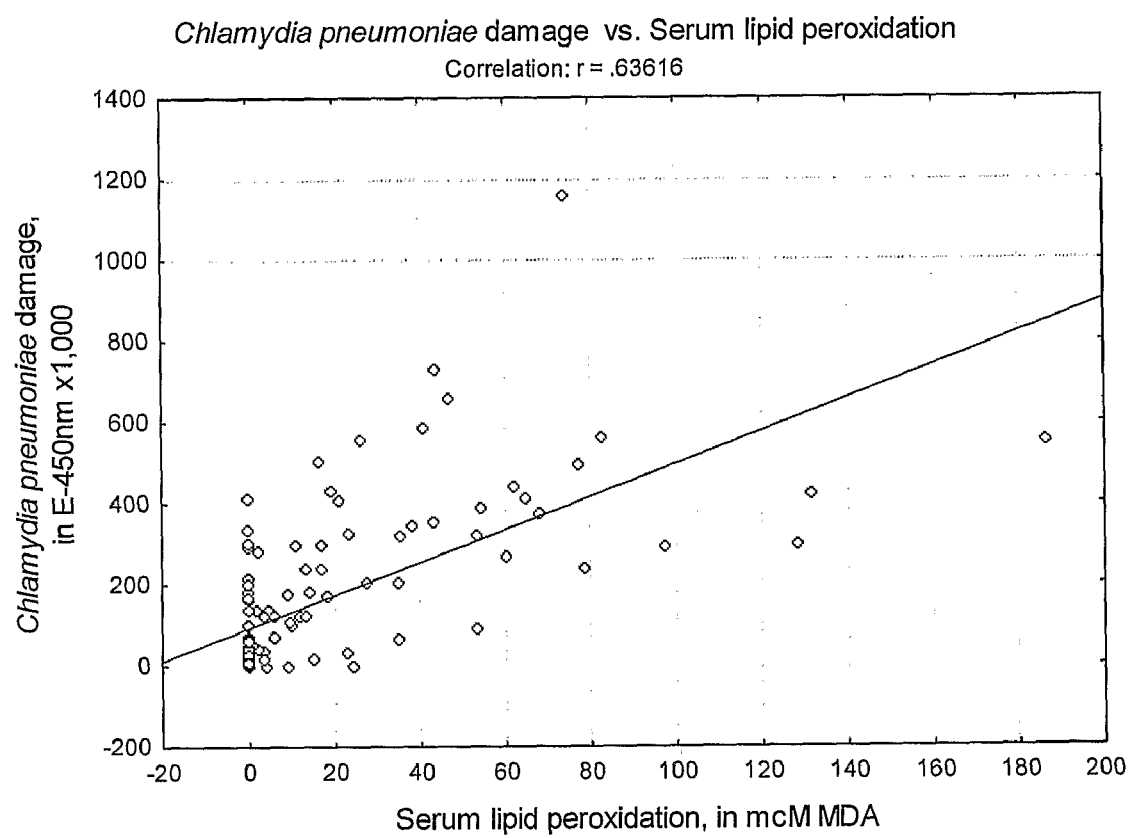

FIG. 1 shows an assay of *Chlamydia* antigen(s) levels in serum of CHD patients by ELISA as described herein. Dark columns are aliquots of serum where abzymes were inactivated, light columns are untreated aliquots. *Chlamydia* antigen was detected in concentrations of more than 1 μg per ml of serum in 14 out of 21 samples from patients with CHD. 0.1 $E_{450nm}$=2 μg of *Chlamydia* LPS, starting from the Cut-off level of 0.2 $E_{450nm}$ FIG. 2 shows a comparison of lipid oxidation and *Chlamydia* antigen damage assays to measure the activity of anti-*Chlamydia* abzymes.

Table 1 shows a comparison of antibody measurement by ELISA in samples of patient sera, in healthy individuals, individuals with respiratory disorders and individuals with Coronary Heart Disease & Cerebral Atherosclerosis, where some of them were treated for abzyme inactivation but the others remained untreated.

Table 2 shows a comparison of antibody measurement by ELISA in treated and untreated samples of patient sera, in healthy individuals, individuals with respiratory disorders and individuals with Coronary Heart Disease & Cerebral Atherosclerosis.

Table 3 shows the effect of lipid oxidation inactivation on the results of MIF testing on anti-*Chlamydia pneumonia** antibodies IgG in human sera.

Table 4 shows the activity of various compounds in inactivating antibody mediated lipid oxidation activity.

EXAMPLES

Materials and Methods

Preparation of Samples

Blood samples were obtained from healthy individuals, individuals suffering from respiratory disorders and individuals with coronary heart disease & cerebral atherosclerosis.

Serum was isolated by centrifugation and stored at −20° C. for not more than three months. After thawing, samples were tested either immediately or within 24 hours.

Inactivation of Lipid Oxidation Activity

For physical inactivation, the same sample was split into two aliquots. One aliquot was heated in a water bath for 30 minutes at 56° C. The other was untreated. Following treatment of the first aliquot, both samples are taken and tested in the same fashion.

For chemical inactivation, a diluent solution was divided into two portions. In one portion, an abzyme inhibitor was added. The following abzyme inhibitors were used DMSO, 0.1-10%; sodium azide, $10^{-5}$-$10^{-3}$M; catechins, $10^{-6}$-$10^{-3}$M; ketek, $10^6$-$10^{-3}$M; lactobacilli culture, 1 μM-1 mM; ascorbic acid, $10^{-4}$-$10^{-3}$M; acetyl salicylic acid, $10^{-4}$-$10^{-3}$M.

The serum sample was split in two aliquots and one aliquot was diluted by solution containing the abzyme inhibitor, the second aliquot was diluted by the control solution. The aliquots were then tested in the same fashion.

ELISA Assay

ELISA assays were performed using Medac materials and reagents, which were used in accordance with the manufacturers instructions.

Briefly, serum samples from patients were treated as described above. 50 μl of sample diluent was pipetted into microtitre well A1 as blank, and 50 μl of the negative control, Positive Control and the diluted patients' samples were pipetted into other microtitre wells. The microplate wells were incubated for 60 min (±5 min) at 37° C. (±1° C.) in a humid chamber and then washed three times with 200 μl wash buffer per well. 50 μl of Conjugate was then added to each well and the microplate wells incubated again for 60 min (±5 min) at 37° C. (±1° C.) in a humid chamber and then washed. 50 μl of TMB-Substrate, was added to each well and the microplate wells incubated for 30 min (±2 min) at 37° C. (±1° C.) in a humid chamber. The reaction was stopped by adding 100 μl of Stop Solution, to each well.

Photometric reading was performed using a plate reader at 450 nm (ref. 620-650 nm) within 15 min after adding the Stop Solution.

To calculate the results, the OD value of the blank (well A1) was subtracted from all other OD values. Preferably, the OD value of the blank was <0.150, the mean OD value of the Negative Control was <0.100 and the OD value of the Positive Control was >0.800. Cut-off=mean OD value of the Negative Control+0.380. Grey zone=Cut-off±10%

MIF Assay

Slides with antigens of *Chlamydia trachomatis*, *C. psittaci*, and *C. pneumoniae* were prepared by applying purified elementary bodies of these bacteria.

Sera were diluted to a titer of 1:1024 in phosphate-buffered saline (PBS) and incubated for 30 min at 37° C. After washing in PBS, anti-human IgG, IgA, IgM conjugates were added to the samples. After 30 mins of incubation at 37 C and being washed in PBS, the slide was covered with a cover slip with mounting medium. A fluorescent microscope was used for the reading of the slides. A positive reaction is represented by a "starry sky" appearance: fluorescent green spots on a slightly red background. All samples were evaluated by two independent experts.

Electron Microscopy on Lysed *Chlamydia*

Bacteria cells were fixed for 1 hour in 2.5% solution of glutaraldehyde, made in 0.2 M cacodylic buffer pH 7.2, after that in chrome-osmium solution for another hour. After that, samples were dehydrated in a gradient increase of ethanol and absolute acetone and imbedded in Eponate 12T14-Araldite 502. Ultra-thin slides were made by using Ultracut Reichert-Jung, stained by 1% water solution of uranyl acetate and lead citrate.

Slides were examined and photographed using an electron microscope JEM 100C×(with magnification of)×5300-53000 times.

SDS-PAGE

Polyacrylamide gel electrophoresis was performed using various commercially available systems, in accordance with the manufacturer's instructions. For example, the method described in DPO 033/02; Issue 1.0 "Protein electrophoresis using NOVEX™ system (SDS-PAGE)" was used with the following reagents: NuPAGE™ Bis-Tris 4-12% precast gels (Invitrogen NP0321 batch #2063076) (15 well); NuPAGE™ Bis-Tris 4-12% precast gels (Invitrogen NP0321 batch #2072272) (10 well); NuPAGE™LDS sample buffer 4×(Invitrogen NP0007 batch #300277); NuPAGE™ Sample reducing agent×10 (Invitrogen NP0004 batch #300505) NuPAGE™ MOPS SDS running buffer×20 (Invitrogen NP0001 batch #300704); SeeBlue™ pre stained markers (Invitrogen LC5625 batch #see11214).

Determination of Peroxidation of Lipids

Lipid peroxidation was assessed as a level of MDA concentration which was measured by spectrophotometric method [Draper, H. H. et al Free Radic. Biol. Med. (1993) 15, 353]. This method is based on the formation of a coloured product when malondialdehyde reacts with thiobarbituric acid. Briefly, the level of abzymes in a sample was determined as follows: Samples of sera were diluted 1:1 by 0.05M acetate buffer pH 4.0 to make the final pH of these samples between 5.6-5.8. 990 μl of the diluted serum was mixed with 10 μl of the commercial live ovine *Chlamydia* vaccine (Intervet). Samples were incubated overnight (12-16 hours) at 37° C. 250 μl of 40% trichloroacetic acid and 250 μl of 1 mM 2-thiobarbituric acid was added to each sample. All samples were placed in a water bath and boiled for 30 minutes. Samples were cooled down and centrifuged at 3,000 g for 10 minutes. The supernatants were collected and their absorption measured at λ 525 nm to determine the concentration of malondialdehydes (MDA), which are products of lipid peroxidation.

Results

Antibody Tests
ELISA

Antibodies were measured by ELISA as described above in samples of patient sera. The results are shown in Tables 1 and 2.

These results show that inhibition of the abzymes increased antigen binding in some of the positive samples in the control group, but did not affect antigen binding significantly in the sera of the patients with respiratory diseases.

However, the abzyme inactivation made a significant impact on the detection of the specific anti-*Chlamydia* antibodies in the serum of the patients with clinical complications of atherosclerosis. A significant activity of anti-*Chlamydia* abzymes can usually be detected there.

Inactivation of the abzymes was accompanied by shifting of the results from the "grey zone" level, or "mildly positive", for the overwhelming majority of the tested samples, to "strongly positive" reading with absorption of more than 1.0. If, before such treatment, the percentage of strongly positive serum samples was 18%, after abzyme inactivation it became 61%.

MIF

A similar effect of the abzyme inactivation on the measurement of specific anti-*Chlamydia* antibodies was observed in the micro-immunifluorescent assay, MIF (Table 3).

These results indicate that inactivation of abzymes can prevent damage of the antigen(s) used in immunological assays such as ELISA or MIF and thus provide a more accurate measurement of the level of specific antibodies present in analysed samples.

Antigen Tests
ELISA

Results of the measurement of *Chlamydia* antigens in the serum of patients with Coronary Heart Disease by ELISA, using mouse monoclonal anti-*Chlamydia* LPS antibodies conjugated with Horse Radish Peroxidase, are presented in FIG. 1.

These results show that if serum sample abzymes were not inactivated, only 3 out of 21 samples were positive on the detection of the *Chlamydia* antigens. However, if samples were pre-treated and the abzymes were inactivated, the number of positives became 14.

These results indicate that inactivation of abzymes can prevent damage of the antigen(s) and improve its detection and/or recovery in immunological, immunochemical, immunohistological or other assays and thus provide a more accurate measurement of the level of antigen present in analysed samples.

TABLE 1

| Patient Groups | IgG ELISA, in $E_{450\,nm} \times 1,000$ | | Difference in absorption |
| --- | --- | --- | --- |
| | untreated sera | treated sera | |
| Control | 71 | 79 | 8 |
| | 90 | 83 | 0 |
| | 109 | 104 | 0 |
| | 134 | 150 | 16 |
| | 177 | 171 | 0 |
| | 184 | 247 | 63 |
| | 216 | 186 | 0 |
| | 272 | 234 | 0 |
| | 420 | 400 | 0 |

TABLE 1-continued

| Patient Groups | IgG ELISA, in $E_{450\,nm} \times 1{,}000$ untreated sera | treated sera | Difference in absorption |
|---|---|---|---|
|  | 478 | 521 | 43 |
|  | 517 | 554 | 37 |
|  | 559 | 590 | 31 |
|  | 713 | 1069 | 356 |
|  | 913 | 1150 | 237 |
| Respiratory Disease | 61 | 97 | 36 |
|  | 174 | 143 | 0 |
|  | 174 | 156 | 0 |
|  | 221 | 195 | 0 |
|  | 226 | 211 | 0 |
|  | 236 | 111 | 0 |
|  | 272 | 363 | 91 |
|  | 360 | 381 | 21 |
|  | 416 | 461 | 45 |
|  | 815 | 667 | 0 |
|  | 985 | 924 | 0 |
|  | 1450 | 1416 | 0 |
|  | 1561 | 1586 | 25 |
| Coronary Heart Disease or Cerebral Atherosclerosis | 73 | 87 | 14 |
|  | 194 | 233 | 39 |
|  | 301 | 725 | 424 |
|  | 365 | 544 | 179 |
|  | 446 | 1010 | 564 |
|  | 478 | 771 | 293 |
|  | 538 | 1263 | 725 |
|  | 567 | 1127 | 560 |
|  | 654 | 1713 | 1059 |
|  | 692 | 617 | 0 |
|  | 764 | 1573 | 409 |
|  | 780 | 1078 | 298 |
|  | 781 | 1325 | 544 |
|  | 805 | 1021 | 216 |
|  | 897 | 1542 | 645 |
|  | 988 | 1291 | 303 |
|  | 1022 | 1528 | 506 |
|  | 1175 | 1227 | 52 |

TABLE 2

| Laboratories | Patient Groups | | | | | |
|---|---|---|---|---|---|---|
|  | Control Serum samples | | Respiratory Diseases Serum samples | | Coronary Heart Disease & Cerebral Atherosclerosis Serum samples | |
|  | untreated | treated | untreated | treated | untreated | treated |
| Lab R | 5 (+) | 5 (+) | 2 (+) | 2 (+) | 39 (+) | 47 (+) |
|  | 4 > 1.0 | 4.0 > 1.0 | 2 > 1.0 | 2 > 1.0 | 13 > 1.0 | 41 > 1.0 |
|  | 21% | 21% | 25% | 25% | 24% | 76% |
|  | 2 greys | 2 greys | 1 grey | 0 greys | 11 greys | 4 greys |
|  | 12 (−) | 12 (−) | 6 (−) | 7 (−) | 4 (−) | 3 (−) |
|  | n = 19 | | n = 8 | | n = 54 | |
| Clinical Lab | 3 (+) | 4 (+) |  |  | 23 (+) | 27 (+) |
|  | 0 > 1.0 | 0 > 1.0 |  |  | 2 > 1.0 | 11 > 1.0 |
|  | 0% | 0% |  |  | 8.7% | 41% |
|  | 0 greys | 2 greys |  |  | 5 greys | 4 greys |
|  | 9 (−) | 6 (−) |  |  | 4 (−) | 1 (−) |
|  | n = 12 | | | | n = 32 | |
| CTL Lab | 1 (+) | 2 (+) | 6 (+) | 6 (+) | 45 (+) | 55 (+) |
|  | 0 > 1.0 | 0 > 1.0 | 3 > 1.0 | 3 > 1.0 | 13 > 1.0 | 43 > 1.0 |
|  | 0% | 0% | 19% | 19% | 19% | 61% |
|  | 3 greys | 2 greys | 9 greys | 5 greys | 14 greys | 5 greys |
|  | 10 (−) | 10 (−) | 1 (−) | 5 (−) | 11 (−) | 10 (−) |
|  | n = 14 | | n = 16 | | n = 70 | |
| Total | 9 (+) | 11 (+) | 8 (+) | 8 (+) | 107 (+) | 129 (+) |
|  | 20% | 24% | 32% | 32% | 67% | 82% |
|  | 4 > 1.0 | 4 > 1.0 | 5 > 1.0 | 5 > 1.0 | 28 > 1.0 | 95 > 1.0 |
|  | 8.9% | 8.9% | 20% | 20% | 18% | 61% |
|  | 5 greys | 6 greys | 10 greys | 5 greys | 31 greys | 14 greys |
|  | 31 (−) | 28 (−) | 7 (−) | 12 (−) | 19 (−) | 14 (−) |
|  | n = 45 | | n = 25 | | n = 157 | |

Lab R and Clinical Lab are collaborating with CTL laboratories.

TABLE 3

MIF test, in titers

| Serum ID | Untreated serum samples (abzymes detected) | | Treated serum samples (abzymes non-detected) |
|---|---|---|---|
| Abzyme positive | | | |
| 285 GAZ | 32/64 | < | 512/512 |
| 286 TGB | 32/64 | ≦ | 64/64 |
| 288 VPK | 16/32 | < | 64/64 |
| 297 NEC | 32/64 | < | 128/128 |
| 302 IVK | 16/32 | < | 64/64 |
| 305 VNX | 16/32 | < | 64/64 |
| P577 | 0 | < | 1/128 |
| OAG | 0 | < | 1/64 |
| YIO | 0 | < | 1/64 |
| IVM | 0 | < | 1/64 |
| IMK | 0-1/16 | < | 1/64 |
| P580 | 0 | < | 1/64 |
| P573 | 0 | < | 1/64 |
| P571 | 0 | < | 1/32 |
| AFP | 0 | < | 1/16-1/32 |
| VAM | 0 | < | 1/16 |
| P572 | 0 | = | 0 |
| Abzyme-negative | | | |
| 282 AVS | 32/32 | < | 64/64 |
| 287 VAG | 32/64 | ≦ | 64/64 |
| 289 VPK | 256/1024 | ≦ | 1024/1024 |
| 292 VLC | 64/128 | < | 256/512 |
| 294 YIX | 32/32 | = | 32/32 |
| 298 VAP | 0/0 | = | 0/0 |
| P585 | 0 | = | 0 |
| AIS | 0 | = | 0 |
| GPM | 0 | = | 0 |
| P567 | 0 | = | 0 |
| INK | 0 | = | 0-1/16 |
| SII | 0 | = | 0-1/16 |
| NEC | 0 | = | 0 |
| JON | 0 | = | 0-1/16 |
| KAT | 0 | = | 0 |
| JIM | 0 | = | 0 |

*Purified Iol and Kajaani 6 strains of *Chlamydia pneumonia* were used

TABLE 4

| Factors affecting abzyme activity | Inhibition of abzymes ability to cause: | |
|---|---|---|
| | Serum lipid peroxidation, in MDA assay | Damage of *Chlamydia pneumoniae* antigen, in ELISA |
| Physical procedures | | |
| Repetitive freezing thawing | Positive | Positive |
| Heating at 56° C. for 30 min | Positive | Positive |
| Drugs, reagents or food products | | |
| 1. Acetyl salicylic acid | Positive | Positive |
| 2. Ascorbic acid | Positive | Positive |
| 3. EDTA | Positive | Positive |
| 4. EGTA | n/a | Positive |
| 5. Sodium cyanide | Negative | Negative |
| 6. Sodium azide | Positive | Positive |
| 7. (+) Catechin gallate | Positive | Positive |
| 8. β-Carotene | Negative | Negative |
| 9. (+) α-Tocopherol | Negative | Negative |
| 10. (+) γ-Tocopherol | Negative | Negative |
| 11. Benzoic acid | Negative | Negative |
| 12. DMSO | Positive | Positive |
| 13. D-Mannitol | Negative | Negative |
| 14. PMS | Negative | Negative |
| 15. Haemoglobin | Positive | Positive |
| 16. Telithromycin, Ketek | Positive | Positive |
| 17. Tetracycline | Negative | Negative |
| 18. Lactobacilli culture | Positive | Positive |
| 19. Lycopene | Negative | Negative |

* antibody-antigen reaction was blocked by lowered pH after addition of these acid compounds.

The invention claimed is:

1. A method of measuring the amount of a first *Chlamydia* binding pair member in a sample comprising;
   providing a sample in which the amount of first *Chlamydia* binding pair member is to be measured,
   abrogating lipid oxidation activity in said sample without affecting the binding properties of the *Chlamydia* binding pair member,
   providing a second *Chlamydia* binding pair member,
   contacting the treated sample with the second *Chlamydia* binding pair member, and
   determining the amount of binding of a first *Chlamydia* binding pair member in the treated sample to the second *Chlamydia* binding pair member,
   the amount of binding after said treatment being indicative of the level of the first *Chlamydia* binding pair member in the sample,
   wherein the first *Chlamydia* binding pair member is a *Chlamydia* antigen and the second *Chlamydia* binding pair member is an anti-*Chlamydia* antibody; or
   wherein the first *Chlamydia* binding pair member is an anti-*Chlamydia* antibody and the second *Chlamydia* binding pair member is a *Chlamydia* antigen.

2. The method according to claim 1 wherein the sample is obtained from an individual and the level of the first *Chlamydia* binding pair member in the sample is indicative of *Chlamydia* infection in said individual.

3. The method according to claim 2 wherein the sample is a serum sample obtained from said individual.

4. The method according to claim 1 wherein the sample is physically treated to inactivate lipid oxidation activity.

5. The method according to claim 4 wherein the sample is heated.

6. The method according to claim 5 wherein the sample is heated to at least 37° C. for at least 5 minutes.

7. The method according to claim 6 wherein the sample is heated to 56° C. for 30 mins.

8. The method according to claim 4 wherein the sample is exposed to two or more freeze thaw cycles.

9. The method according to claim 4 wherein the sample is maintained at 0° C. to 4° C. for 4-7 days.

10. The method according to claim 1 wherein the sample is chemically treated to inactivate abzymes.

11. The method according to claim 10 wherein the sample is treated with one or more inactivating agents.

12. The method according to claim 11 wherein the inactivating agent is a hydroxyl radical scavenger, low pH antioxidant, electron trapper, cushion or sink.

13. The method according to claim 10 wherein the inactivating agent is selected from the group consisting of ascorbic acid, acetyl salicylic acid, sodium azide, (+) catechin gallate, DMSO, haemoglobin and telithromycin ketek or analogues or derivatives thereof.

14. The method according to claim 11 wherein the inactivating agent is a bacterial cell.

15. The method according to claim 14 wherein the inactivating agent is a lactobacillus cell.

16. The method according to claim 1 wherein the abzyme mediated lipid oxidation of said sample is determined following said abrogation.

17. The method according to claim 1 wherein the sample is further treated to reduce or abrogate complement activity.

18. The method according to claim 1 wherein the second *Chlamydia* binding pair member is immobilised.

19. The method according to claim 1 wherein the second *Chlamydia* binding pair member is labelled.

20. A method according to claim 1 wherein the second *Chlamydia* binding pair member is labelled with a detectable reporter molecule.

21. The method according to claim 1 wherein the *Chlamydia* antigen is on the surface of a *Chlamydia* cell.

22. The method according to claim 1 wherein the binding of the second *Chlamydia* binding pair member to the first *Chlamydia* binding pair member is determined using a second antibody.

23. The method according to claim 22 wherein the second antibody is an anti-*Chlamydia* antibody or an anti-IgG antibody.

24. The method according to claim 22 wherein the second antibody is labelled.

* * * * *